US012642963B2

(12) United States Patent
Wang et al.

(10) Patent No.: US 12,642,963 B2
(45) Date of Patent: Jun. 2, 2026

(54) WRISTBAND NERVE STIMULATOR APPLICABLE TO BOTH LEFT AND RIGHT HANDS AND USE METHOD THEREOF

(71) Applicants: Fasikl Incorporated, Dallas, TX (US); Hangzhou Fasikl Technology Co., Ltd, Hangzhou (CN)

(72) Inventors: Baitong Wang, Hangzhou (CN); Bing Ye, Hangzhou (CN); Linh Hoang, Dallas, TX (US); Markus Drealan, Dallas, TX (US)

(73) Assignees: Fasikl Incorporated, Dallas, TX (US); Hangzhou Fasikl Technology Co., Ltd., Hangzhou (CN)

( * ) Notice: Subject to any disclaimer, the term of this patent is extended or adjusted under 35 U.S.C. 154(b) by 569 days.

(21) Appl. No.: 18/121,024

(22) Filed: Mar. 14, 2023

(65) Prior Publication Data

US 2023/0218897 A1     Jul. 13, 2023

(30) Foreign Application Priority Data

Apr. 1, 2022    (CN) .......................... 202210337333.8

(51) Int. Cl.
*A61N 1/36* (2006.01)
*A61N 1/04* (2006.01)

(52) U.S. Cl.
CPC ......... *A61N 1/3603* (2017.08); *A61N 1/0456* (2013.01); *A61N 1/0484* (2013.01)

(58) Field of Classification Search
CPC .. A61N 1/3603; A61N 1/0456; A61N 1/0484; A61N 1/0452; A61N 1/0492; A61N 1/36014; A61N 1/36034; A61N 1/36003
See application file for complete search history.

(56) References Cited

U.S. PATENT DOCUMENTS

| | | | |
|---|---|---|---|
| 2012/0203245 A1 | 8/2012 | Imabayashi et al. | |
| 2014/0235955 A1* | 8/2014 | Rao .......................... | A61B 5/00 600/300 |
| 2017/0259061 A1 | 9/2017 | Simon et al. | |
| 2018/0326205 A1* | 11/2018 | Cheng ................ | A61N 1/36021 |
| 2020/0346008 A1 | 11/2020 | Song | |

* cited by examiner

*Primary Examiner* — Amanda L Steinberg
*Assistant Examiner* — Philip C Edwards
(74) *Attorney, Agent, or Firm* — Hemisphere Law, PLLC

(57) ABSTRACT

The present disclosure discloses a wristband nerve stimulator applicable to both the left and right hands and a use method thereof. The wristband nerve stimulator includes a fixed main unit and an electrode piece band; a groove and an adapter port are respectively arranged on two sides of a bottom of the fixed main unit; a controller is arranged in the fixed main unit; the controller includes a main control unit (MCU), an intelligent identification unit, a storage unit and a stimulation unit; the electrode piece band comprises a base and an electrode assembly; adapter seats are arranged on two sides of a top surface of the base; a memory IC is arranged in the base; the memory IC is provided with an independent identification ID and can record the number of use or the service life of the electrode piece band.

9 Claims, 10 Drawing Sheets

WRISTBAND NERVE STIMULATOR APPLICABLE TO BOTH LEFT AND RIGHT HANDS AND USE METHOD THEREOF

TECHNICAL FIELD

The present disclosure relates to the technical field of medical instruments, specifically to a wristband nerve stimulator applicable to both left and right hands and a use method thereof.

BACKGROUND

A wristband nerve stimulator is small-sized wearable electrical stimulation equipment, which is worn on the wrist. The median nerves, the radialis nerves and/or the ulnar nerves distributed in the hand according to a certain rule through electrode sheets clung around the wrist. Generally, the tremor strength of user's left and right hands is first evaluated through a tremor testing method. The wristband nerve stimulator is worn on the hand that has higher tremor strength. If the two hands have the same tremor, the wristband nerve stimulator is worn on the hand that is used usually. A band electrode usually does not have no long service life and needs to be replaced within the expiration period to ensure the best treatment effect.

An electrode piece band with matched stimulation strength and of a corresponding specification is selected according to doctor's guidance to perform electrotherapy on the left hand or right hand, which can achieve the best treatment effect. The wristband nerve stimulator in the prior art has no simple and visualized wearing guidance, which easily causes a user to do misoperations and delay the timing of treatment. When the electrodes of the band are expired and need to be replaced, the equipment cannot remind the user in advance, and the user cannot replace the electrodes in time and will still use the expired electrodes, which will seriously affect the treatment effect. ID identification cannot be applied to an unmatched electrode piece band which will affect the treatment effect, and even seriously has potential safety hazard. The existing equipment cannot be applied to both the left and right hands, and is poor in compatibility.

SUMMARY

The present disclosure aims to provide a wristband nerve stimulator applicable to both the left and right hands and a use method thereof, and solves the problems in the background section.

In order to achieve the above objective, the present disclosure provides the following technical solution: A wristband nerve stimulator applicable to both the left and right hands, including:

a fixed main unit, wherein a groove and an adapter port are respectively arranged on two sides of a bottom of the fixed main unit; a controller is arranged in the fixed main unit; the controller at least includes a main control unit (MCU), a storage unit and a stimulation unit; and an electrode piece band, wherein the electrode piece band includes a base and an electrode assembly; adapter seats are arranged on two sides of a top surface of the base; the shapes of the two adapter seats are matched with the shapes of the groove and the adapter port.

Preferably, a plurality of PIN points are arranged in the adapter port; the controller is electrically connected to the plurality of PIN points; and the controller further includes an intelligent identification unit.

Preferably, a memory IC is arranged in the base; the two adapter seats are electrically connected with the memory IC; an independent identification ID is arranged in the memory IC; the electrode assembly is provided with a plurality of electrode pieces; the two adapter seats are electrically connected with the plurality of electrode pieces; and a plurality of pins matched with the PIN points are arranged on the adapter seats.

Preferably, a plurality of first magnetic attraction blocks are arranged at the bottom of the fixed main unit; the plurality of first magnetic attraction blocks are respectively located on front and rear sides of the groove and front and rear sides of the adapter port; and a plurality of second magnetic attraction blocks matched with the first magnetic attraction blocks are arranged on the base.

Preferably, a plurality of PIN points are arranged in the adapter port; a plurality of pins are arranged on the adapter seats; and the fixed main unit is electrically connected with the electrode piece band through contact between the PIN points and the pins.

Preferably, the MCU is NRF52840, and the memory IC is DS2431Q.

Preferably, the intelligent identification unit is configured to identify the identification ID in the memory IC to monitor the number of use or a service life of the electrode piece band.

Preferably, the fixed main unit is also provided with a display screen, a control button and a charging interface.

Preferably, the wristband nerve stimulator further includes a regulation band, and two ends of the regulation band are movably connected with two sides of the fixed main unit respectively.

A use method of the wristband nerve stimulator applicable to both the left and right hands includes:

S1: the adapter seat on one side is embedded in the adapter port; the adapter seat on the other side is embedded in the groove; the first magnetic attraction blocks and the second magnetic attraction blocks are connected in an attracting manner, so that the fixed main unit and the electrode piece band are quickly mounted; the PIN points and the pins are connected with each other in a resisting manner, so that the fixed main unit and the electrode piece band are electrically connected;

S2: the intelligent identification unit can identify connection pins of the controller and the memory IC, and determines a connection direction of the electrode piece band according to preset parameters of the fixed main unit; if the connection direction is correct, the fixed main unit and the electrode piece band can be used normally; if the connection direction is wrong, the fixed main unit and the electrode piece band cannot be used, and the fixed main unit continuously sends a warning signal and can be used normally until the connection direction is turned;

S3: the intelligent identification unit also detects the independent identification ID in the memory IC, compares a parameter in the storage unit with the identification ID, and determines whether the electrode piece band is a matched electrode piece band; if the electrode piece band is the matched electrode piece band, the fixed main unit and the electrode piece band can be used normally; if the electrode piece band is not a matched electrode piece band, the fixed main unit and the electrode piece band cannot be used, and the fixed main unit continuously sends a warning signal and can be used normally until the matched electrode piece band is replaced; the memory IC can be configured to record the number of use or service life of the electrode piece band; if the number of use or service life exceeds a preset number of use or service life, the fixed main unit cannot be used, and can be used normally only after a qualified electrode piece band is replaced;

S4: the wrist of a user passes through a ringlike opening between the fixed main unit and the regulation band, and the ringlike opening is regulated by the regulation band for wearing, so that the electrode pieces on the electrode piece band are fully fitted to the skin of the user; and S5: the fixed main unit is controlled by a human-machine interface on the fixed main unit to output a current to the electrode piece band, and the electrode pieces generate a current to perform electrotherapy on the user.

Compared with the prior art, the present disclosure has the following beneficial effects.

1. By the arrangement of the memory IC, when the electrode piece band and the fixed main unit are used, use data of the electrode piece band can be recorded and saved in real time through the memory IC. When the electrode piece band is about to be expired, the wristband nerve stimulator can remind a user of timely replacement. If the expired electrode piece band is still used, the fixed main unit is locked, and the fixed main unit can be continued to be used normally only after a new electrode piece band is replaced. The identification ID in the memory IC can be monitored by the intelligent identification unit, so as to ensure that the electrode piece band is a matched electrode piece band and guarantees the effectiveness and safety of use of the user.

2. By the arrangement of the controller, when the electrode piece band and the fixed main unit are connected, the intelligent identification unit can determine the connection direction of the electrode piece band according to the connection pins of the controller and the memory IC, that is, the adapter port is connected to the adapter seat on the left or the adapter seat on the right; connection pin data is stored through the storage unit; when the connection pin of the memory IC is matched with the pin data, the fixed main unit and the electrode piece band are used normally; when the connection pin of the memory IC and the pin data are not matched, the fixed main unit and the electrode piece band cannot be used, and the fixed main unit sends a fault alarm; a wearing guidance is displayed on the human-machine interface of the screen to instruct the user to mount the device correctly, which guarantees the correctness and safety of use of the user. Furthermore, the storage unit can also store stimulation parameters, and the stimulation unit outputs an appropriate current to the electrode piece band according to the stimulation parameters, so as to ensure a best treatment effect on the user.

3. By means of the groove and the adapter port arranged at the bottom of the fixed main unit and the two adapter seats on the base, the two adapter seats can be steered to be respectively embedded in the adapter port, so that the electrode piece band and the fixed main unit are electrically connected, and the adapter seat embedded in the groove plays a role of insulation, which will not affect the normal use of the wristband nerve stimulator. When the wristband nerve stimulator is worn, the control button on the fixed main unit faces the finger tips, and the electrode piece band can be steered to be connected with the fixed main unit. By the cooperation with the intelligent identification unit, whether the electrode piece band is mounted correctly is determined according to a preset wearing manner of wearing the wristband nerve stimulator on the left hand or the right hand, and the human-machine interface displays corresponding simple and visualized wearing guidance maps to assist the user in quick and correct wearing, thus greatly enhancing the user experience. The fixed main unit and the electrode piece band can be turned around 180° for assembling, so that the wristband nerve stimulator can be worn on both the left and right hands. The wristband nerve stimulator has high universality and is convenient to operate.

4. By the arrangement of the first magnetic attraction blocks and the second magnetic attraction blocks, the two adapter seats are respectively embedded in the adapter port and the groove. The first magnetic attraction blocks and the second magnetic attraction blocks are connected in the attracting manner, so that an effect of quickly mounting and connecting the fixed main unit to the electrode piece band is achieved.

DETAILED DESCRIPTION OF THE EMBODIMENTS

Figure 1:
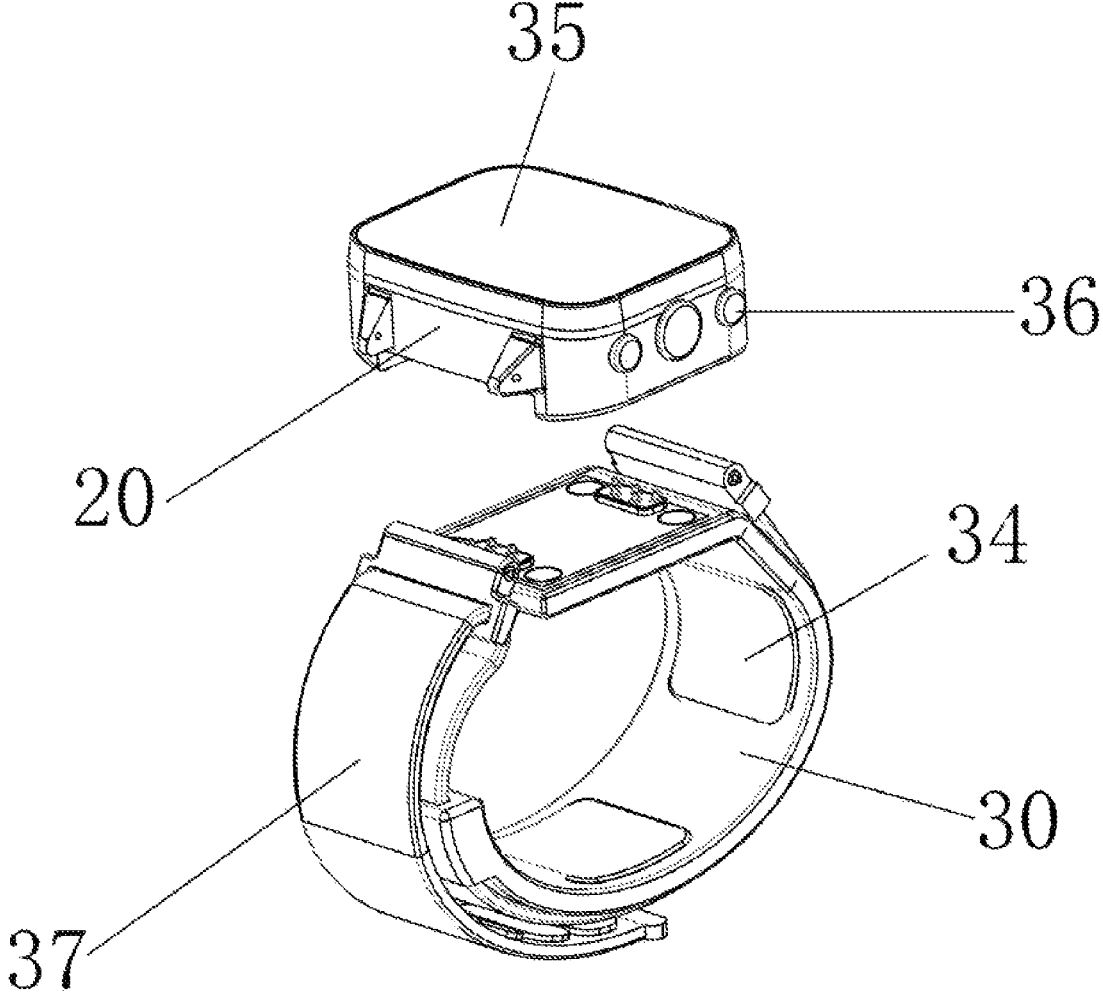
FIG. 1 is a schematic structural diagram of the present disclosure.
Figure 2:
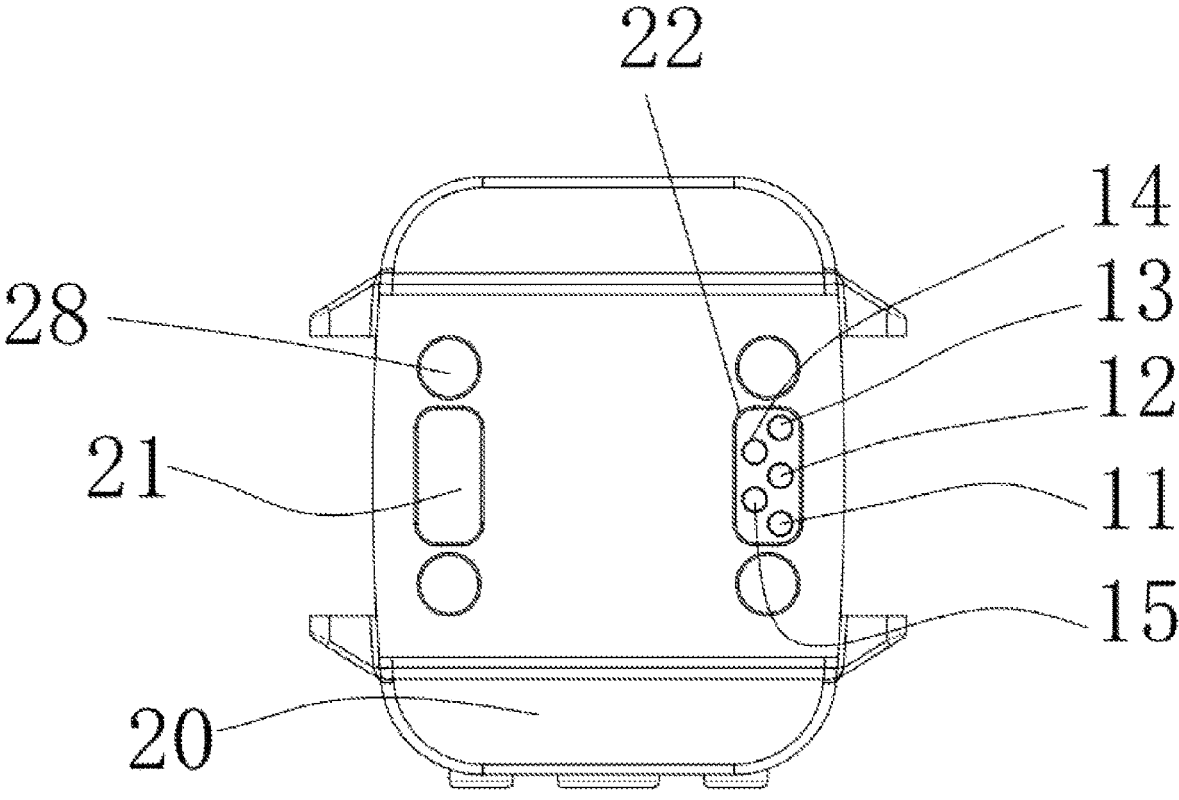
FIG. 2 is a top view of a fixed main unit of the present disclosure.
Figure 3:
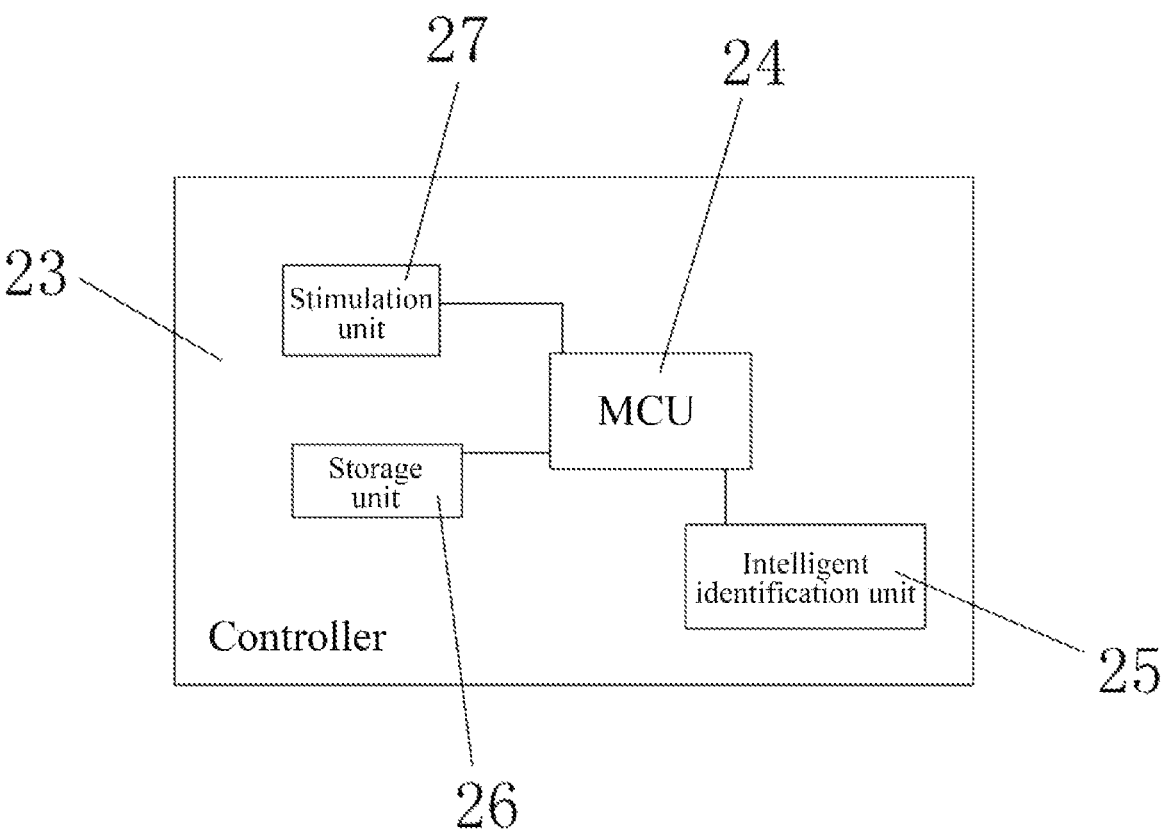
FIG. 3 is a principle block diagram of a controller of the present disclosure.
Figure 4:
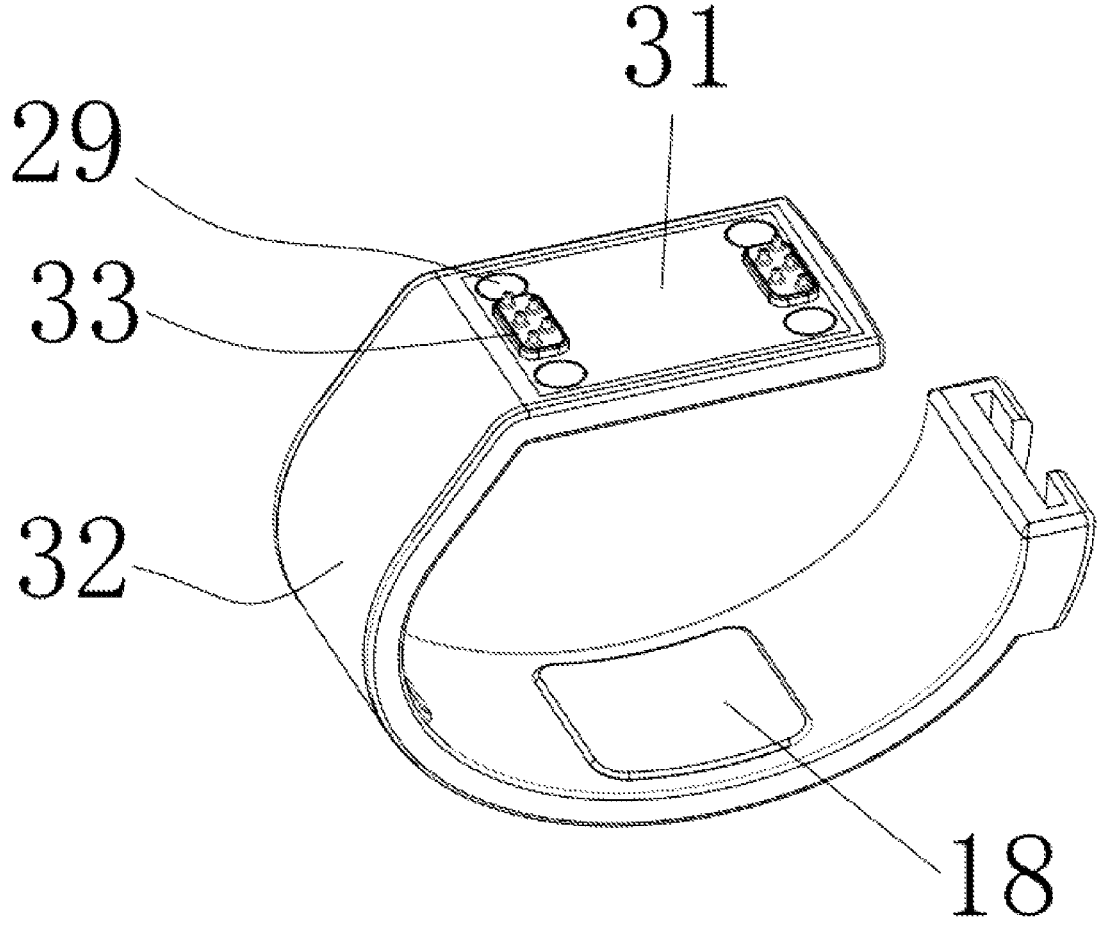
FIG. 4 is a schematic structural diagram I of an electrode piece band of the present disclosure.
Figure 5:
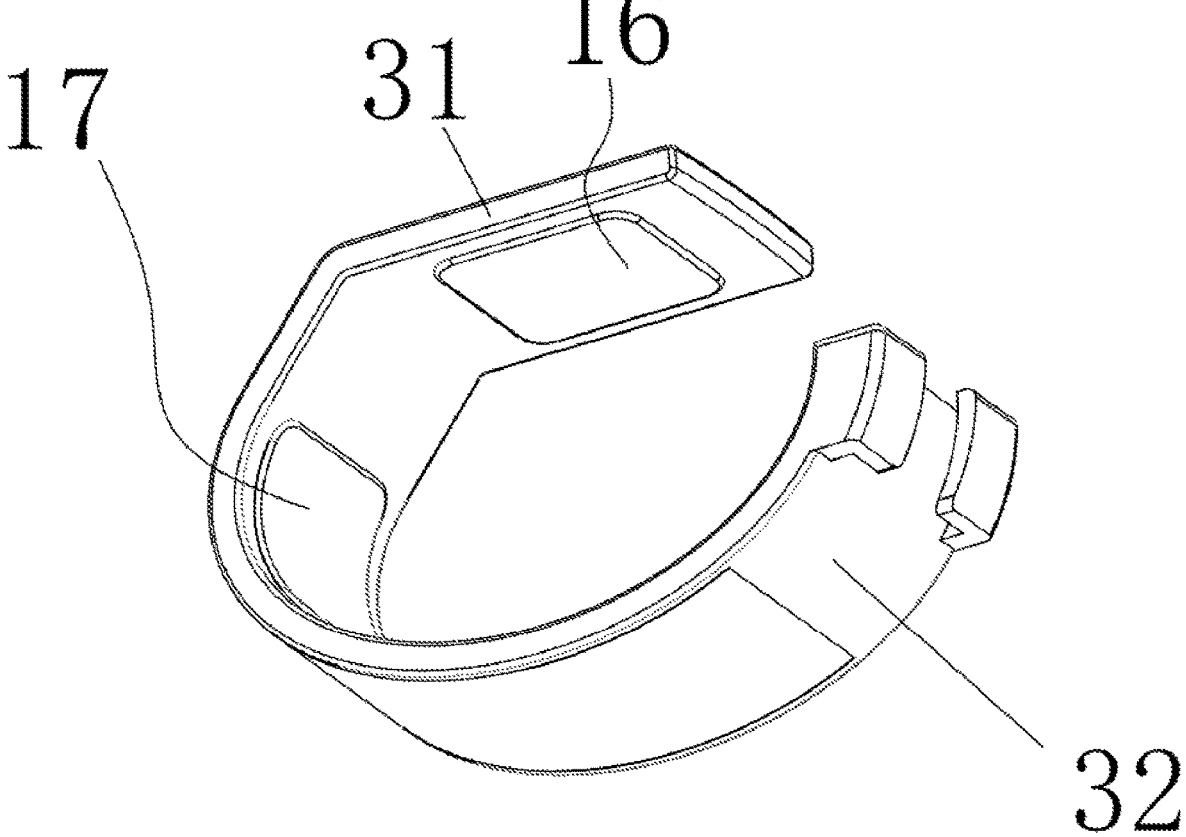
FIG. 5 is a schematic structural diagram II of an electrode piece band of the present disclosure.
Figure 6:
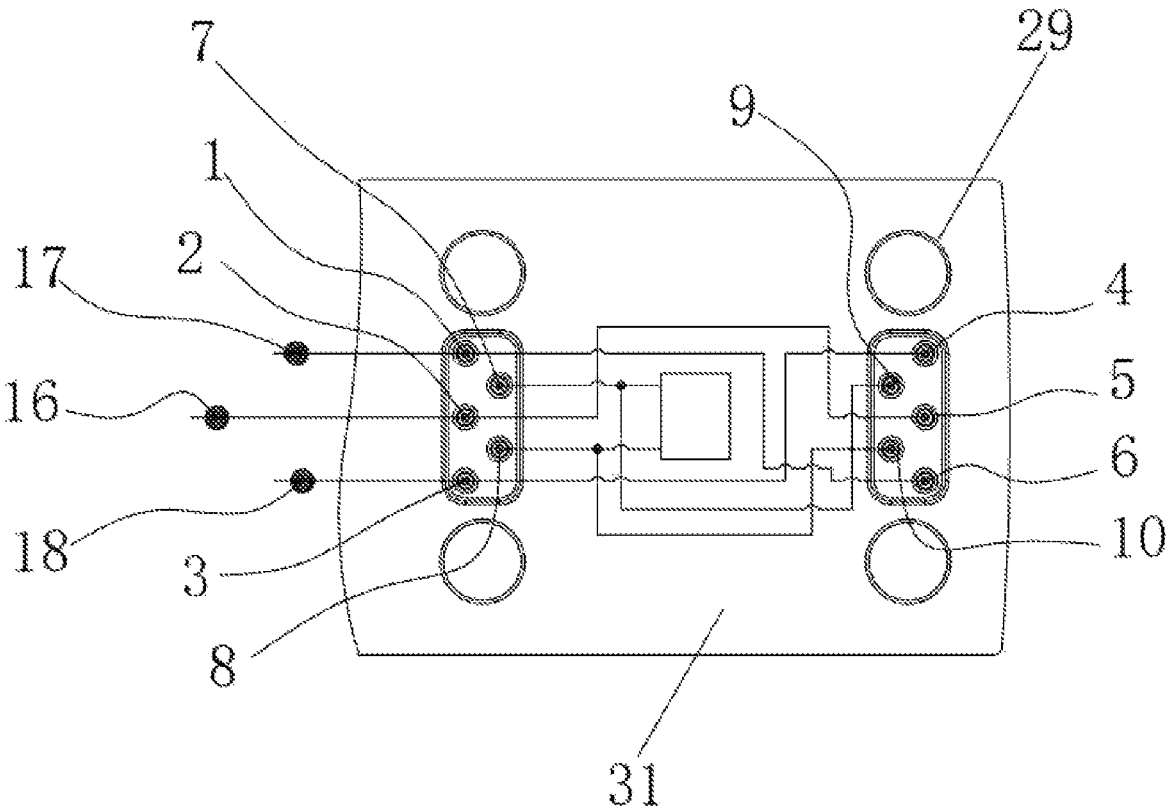
FIG. 6 is a circuit diagram II of an electrode piece band of the present disclosure.
Figure 7:
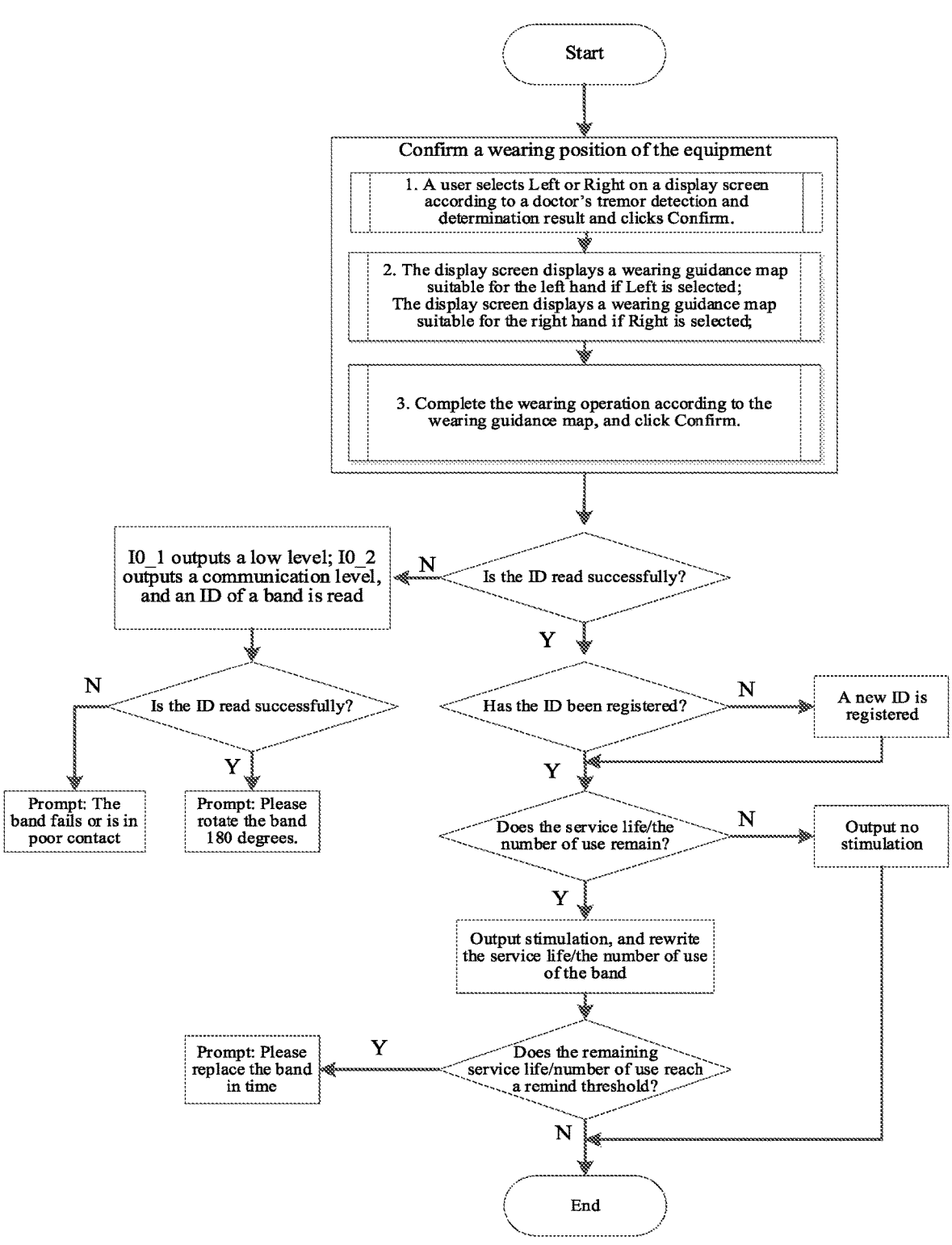
FIG. 7 is a working flow diagram of steps of the present disclosure.

The technical solutions in the embodiments of the present disclosure will be described clearly and completely below in combination with the accompanying drawings of the embodiments of the present disclosure. Apparently, the described embodiments are only part of the embodiments of the present disclosure, not all embodiments. All other embodiments obtained by those of ordinary skill in the art based on the embodiments in the present disclosure without creative work shall fall within the protection scope of the present disclosure.

Referring to FIG. 1 to FIG. 7, an embodiment provided by the present disclosure is shown: A wristband nerve stimulator applicable to both the left and right hands includes a fixed main unit 20 and an electrode piece band 30.

A groove 21 and an adapter port 22 are respectively arranged on two sides of a bottom of the fixed main unit 20. A plurality of PIN points are arranged in the adapter port 22. A controller 23 is arranged in the fixed main unit. The controller 23 is electrically connected with the plurality of PIN points. The controller 23 at least includes an MCU 24, an intelligent identification unit 25, a storage unit 26 and a stimulation unit 27.

The storage unit 26 is configured to store identification data, preset parameters and usage information data, and the stimulation unit 27 is configured to output electrical stimulation, and can adjust the stimulation strength according to the preset parameters in the storage unit 26 and then output electrical stimulation to the electrode piece band 30 through the PIN points in the adapter port 22.

For different types of symptoms, the stimulation unit 27 can output different types of currents according to the preset parameters in the storage unit 26. Different types of currents have different main physiological effects on a user. A direct current is a current with a constant direction, which can change the distribution of ions in the body and adjust the body function. Low and medium-frequency currents stimulate neuromuscular contraction, reduce a pain threshold, and alleviates adhesion. This type of current is often used in neuromuscular diseases, such as injury and inflammation. With its thermal effect on a user, a high-frequency current can promote the circulation, eliminate the inflammation and edema, stimulate tissue regeneration and relieve pain. A high-power high-frequency current can be used for realizing heating and treating cancers. The main function of a static current is to regulate the central nervous system and plant function, and this type of current is often used in neurosis, early hypertension, menopausal syndrome, etc.

The electrode piece band 30 includes a base 31 and an electrode assembly 32. Adapter seats 33 are arranged on two sides of a top surface of the base 31. The shapes of the two adapter seats 33 are matched with the shapes of the groove 21 and the adapter port 22. A memory IC is arranged in the base 31. The two adapter seats 33 are electrically connected with the memory IC, and an independent identification ID is arranged in the memory IC. The electrode assembly 32 is provided with a plurality of electrode pieces 34. The two adapter seats 33 are electrically connected with the plurality of electrode pieces 34, and the adapter seats 33 are provided with a plurality of pins that are matched with the PIN points. When the electrode piece band 30 and the fixed main unit 20 are used, the number of use or service life of the electrode piece band 30 can be recorded and saved in real time through the memory IC. When the electrode piece band 30 is about to be expired, a user can be reminded of timely replacement. If the expired electrode piece band is still used, the fixed main unit 20 will be locked, and can be continued to be used normally after a new electrode piece band 30 is replaced.

Specifically, a plurality of first magnetic attraction blocks 28 are arranged at the bottom of the fixed main unit 20. The plurality of first magnetic attraction blocks 28 are respectively located on front and rear sides of the groove 21 and front and rear sides of the adapter port 22. A plurality of second magnetic attraction blocks 29 matched with the first magnetic attraction blocks 28 are arranged on the base 31. The two adapter seats 33 are embedded in the adapter port 22 and the groove 21 respectively. The first magnetic attraction blocks 28 and the second magnetic attraction blocks 29 are connected in an attracting manner, which achieves an effect of quick mounting and connection between the fixed main unit 20 and the electrode piece band 30.

Specifically, a plurality of PIN points are arranged in the adapter port 22. The plurality of PIN points in this embodiment are pins 11, 12, 13, 14 and 15 respectively. The adapter seats 33 are provided with a plurality of pins. Totally three electrode pieces 34 are provided in this embodiment. The three electrode pieces 34 include a common electrode 16, a radialis nerve electrode 17 and a median nerve electrode 18 respectively. The common electrode 16 is located below the base 31. The radialis nerve electrode 17 is located in a middle portion of the electrode assembly 32. The median nerve electrode 18 is located at the outermost end of the electrode assembly 32. In this example, the adapter seat 33 on the left is provided with five pins including pins 1, 2, 3, 7 and 8. The adapter seat 33 on the right is provided with five pins including pins 4, 5, 6, 9 and 10. Pins 1, 2 and 3 of the adapter seat 33 on the left and pins 4, 5 and 6 of the adapter seat 33 on the right are electrically connected with the radialis nerve electrode 17, the common electrode 16 and the median nerve electrode 18. Pins 7 and 8 of the adapter seat 33 on the left and pins 9 and 10 of the adapter seat 33 on the right are electrically connected with the memory IC respectively. The fixed main unit 20 and the electrode piece band 30 are electrically connected with each other through contact between the PIN points and the pins.

Specifically, the MCU 24 on the controller 23 is NRF52840. This controller 23 has the advantages of small volume, which can effectively save the volume of the fixed main unit when the controller is mounted in the fixed main unit 20. The controller 23 also satisfies the functions of storage of parameters, intelligent identification, current control, human-computer interface control, Bluetooth transmission and the like at the same time. This MCU 24 can achieve the above basic functions, and has the best cost-performance advantage, further optimizing the price of the whole nerve stimulator and improving the competitiveness of the product. The memory IC is DS2431Q, and has the advantage of small volume, which can effectively save the volume of the electrode piece band 30 when the memory IC is mounted in the electrode piece band 30. The memory IC can record the identification ID and the service time. With the cooperation of the fixed main unit 20, the functions of intelligent identification, detection of the service life and the like are realized. This memory IC can achieve the above basic functions, and has the best cost-performance advantage, further optimizing the price of the whole nerve stimulator and improving the competitiveness of the product.

When the wristband nerve stimulator leaves the factory, a unique ID of a specific coding rule is written to the memory IC. The controller 23 reads an ID number in the memory IC through an interface, and decodes it according to the coding rule for ID verification and identification. After the identification succeeds, the service life can be written to the memory IC for saving.

The MCU 24 NRF52840 can be connected to and controls a Bluetooth module (not shown). The Bluetooth module can be wirelessly connected to an electronic device with a Bluetooth function. After being connected to the electronic device, the Bluetooth module can perform wireless data transmission, including updating the ID number, the stimulation parameters, size parameters, and the like in the memory IC in real time, and storing them in the storage unit 26.

The MCU 24 is connected with the intelligent identification unit 25, the storage unit 26 and the stimulation unit 27 through programming by a programmable logic controller (PLC).

The memory IC is provided with two pins including a GND pin and a SI/O pin. During normal operation, GND is required to be at level 0, and SI/O is required to transmit and receive data. The GND pin is connected with pins 8 and 10, and the SI/O pin is connected with pins 7 and 9.

The controller 23 is provided with pins IO_1 and IO_2 (i.e. pins 15 and 14), and the controller 23 can freely configure level states and working modes of IO_1 and IO_2.

Specifically, the intelligent identification unit 25 is configured to identify the identification ID in the memory IC. The intelligent identification unit 25 can determine a connection direction of the electrode piece band 30 according to connection pins of the controller 23 and the memory IC, that is, the adapter port 22 is connected to the adapter seat 33 on the left or the adapter seat 33 on the right; connection pin data is stored through the storage unit 26; when the connection pin of the memory IC is matched with the pin data, the fixed main unit 20 and the electrode piece band 30 are used normally; when the connection pin of the memory IC and the pin data are not matched, the fixed main unit 20 and the electrode piece band 30 cannot be used, and the fixed main unit 20 sends a fault alarm; a wearing guidance is displayed on the human-machine interface of the screen to instruct the user to mount the device correctly, which guarantees the correctness and safety of use of the user.

Furthermore, the intelligent identification unit 25 can detect the identification ID in the memory IC and monitor the number of use or service life of the electrode piece band to ensure that the electrode piece band 30 is original and within the expiration date and guarantee the stability of use. The required electrode piece bands 30 have different resistance values according to different body conditions of different users. The required electrode pieces 34 have different sizes according to different wrist diameters. By means of the identification ID in the memory IC, the intelligent identification unit 25 detects the resistance value, the size and other parameters of the electrode piece band 30, and compares the parameters with preset parameters in the storage unit 26 to determine whether the user uses a matched electrode piece band 34. The best electrotherapy effect is achieved if the matched electrode piece band 30 is selected for electrotherapy.

Specifically, the fixed main unit 20 is also provided with a display screen 35, a control button 36 and a charging interface (not shown). The control button 36 is located on the side of the fixed main unit 20. The charging interface is configured to charge the fixed main unit 20. The display screen 35 is configured to display the human-machine interface of the fixed main unit 20, and corresponding simple and visualized wearing guidance maps can be displayed on the human-machine interface to assist the user in wearing the wristband nerve stimulator quickly and correctly, which greatly improves the user experience. The control button 36 is configured to control the startup or shutdown of the fixed main unit 20 and to realize other auxiliary functions.

When the user wears the wristband nerve stimulator, the control button 36 of the fixed main unit 20 faces the user's finger tips. By this wearing manner, the user can see the control button 36 more intuitively, and control the fixed main unit 20 according to identification on the control button 36, which is more convenient for the user to use the nerve stimulator flexibly and improve the user experience.

Specifically, the wristband nerve stimulator also includes a regulation band 37. Two ends of the regulation band 37 are movably connected with two sides of the fixed main unit 20. The fixed main unit 20 and the regulation band 37 form a ringlike opening. After the user passes through the ringlike opening, the regulation band 37 can adjust the size of the ringlike opening to adapt to the wrist diameter of the user, and the electrode piece band 30 is fitted to an inner wall of the regulation band 37. A plurality of electrode pieces 34 are in contact with the user's skin. The electrode pieces 34 in this embodiment is designed according to the human engineering. Surfaces of the electrode pieces 34 are micro-curved surfaces which are suitable for the radian of the user's wrist, thus further improving the fitness between the electrode pieces 34 and the user's skin, and achieving a better electrotherapy effect.

Figure 8:
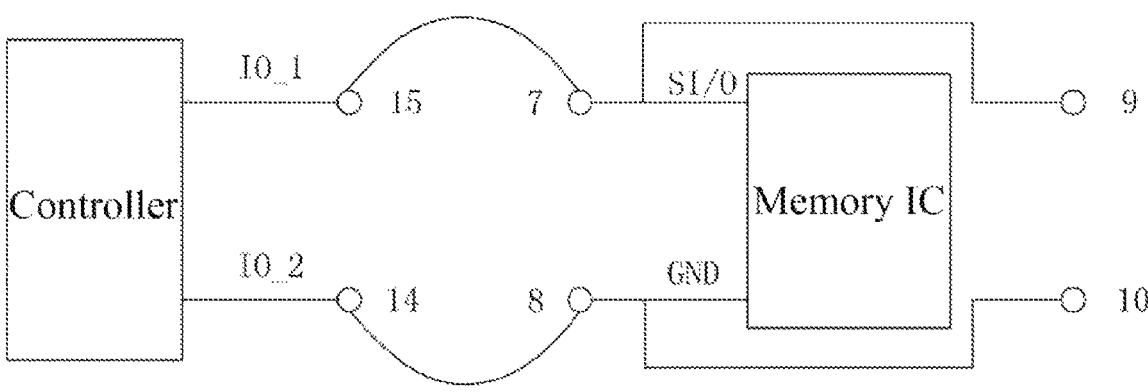
FIG. 8 is a schematic circuit diagram I of a connected state of the present disclosure.
Figure 9:
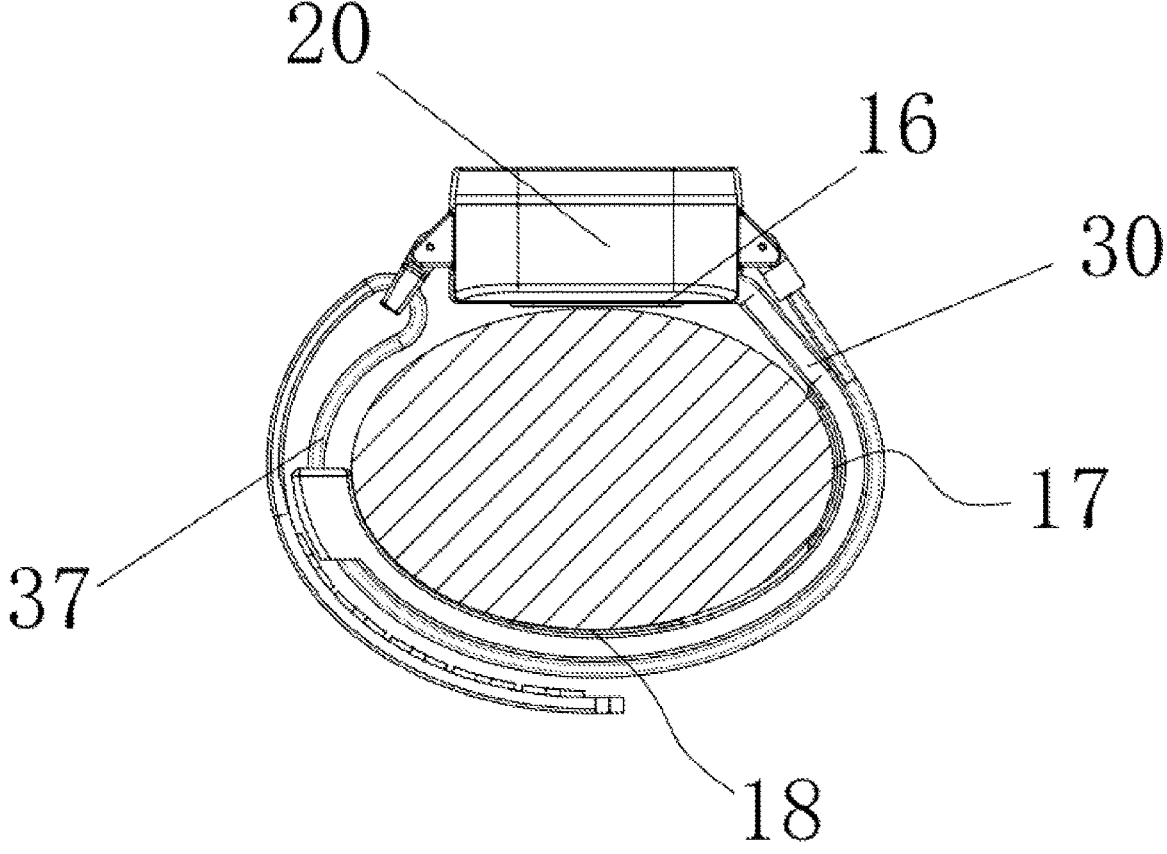
FIG. 9 is a schematic state diagram of wearing on the left hand of the present disclosure.

Referring to FIG. 8 to FIG. 9, a diagram of a wearing state of the wristband nerve stimulator on the left hand is shown. The adapter seat 33 with pins 1, 2, 3, 7 and 8 is embedded in the adapter port 22. Pins 1, 2, 3, 7 and 8 of the adapter seat 33 are respectively connected with pins 11, 12, 13, 15 and 14 of the adapter port 22 in a contact manner. The intelligent identification unit 25 can identify whether the controller 23 is connected with pins 7 and 8 of the adapter seat 33, and ensure that the fixed main unit 20 and the electrode piece band 30 are mounted correctly. The adapter seat 33 with pins 4, 5, 6, 9 and 10 is embedded in the groove 21 and insulated. The electrode piece band 30 is fitted to the right half of the user's wrist.

When the wristband nerve stimulator is worn correctly, pin I0_1 of the controller 23 outputs a level. Pin I0_1 (pin 15) of the controller 23 is connected with the SI/O pin (pin 7) on the memory IC and performs data transmission and receiving. At this time, pin 14 (pin I0_2) of the controller 23 outputs level 0, and the communication is normal, so that it can be determined that the user wears the wristband correctly. When the wristband nerve stimulator is worn incorrectly, pin I0_1 of the controller 23 outputs a level. Pin I0_1 (pin 15) of the controller 23 is connected with the GND pin (pin 8) on the memory IC and performs data transmission and receiving. If the level of the GND pin is not 0, it can be determined that the user wears the wristband incorrectly, and the fixed main unit 20 sends a warning signal at the same time.

Figure 10:
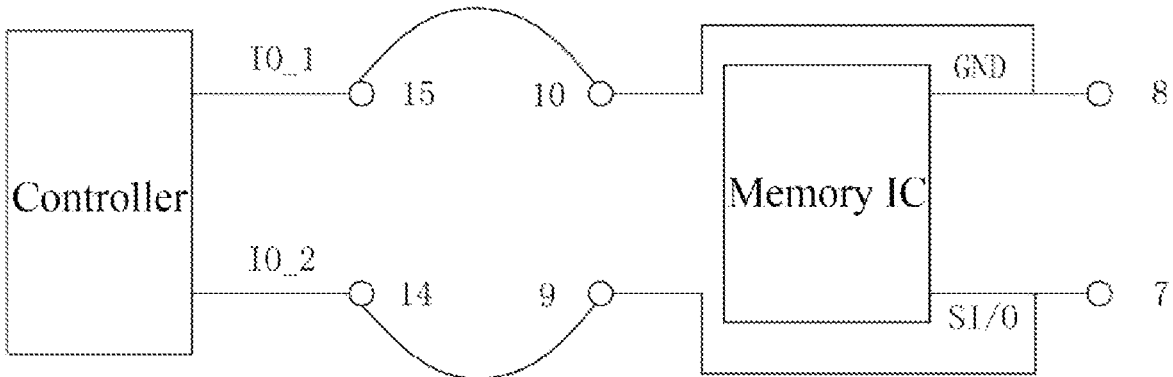
FIG. 10 is a schematic circuit diagram II of a connected state of the present disclosure.
Figure 11:
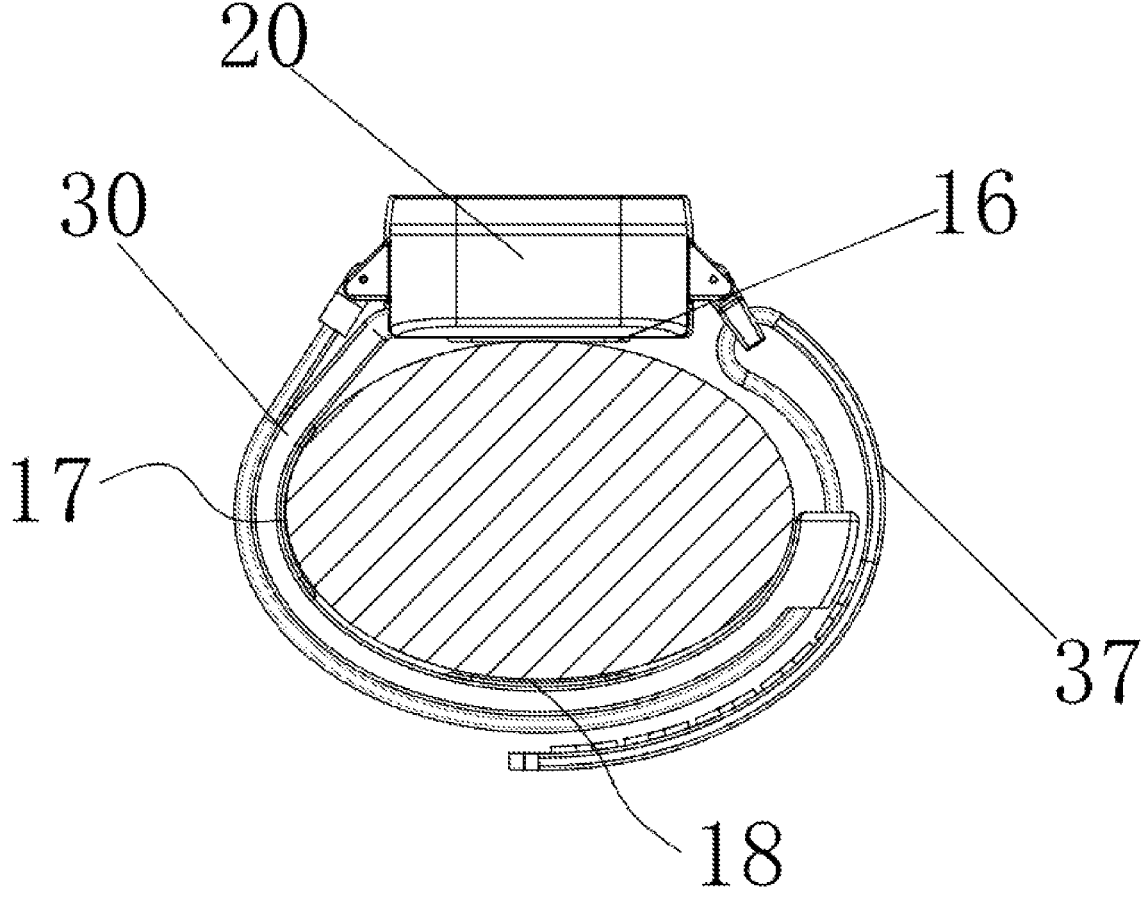
FIG. 11 is a schematic state diagram of wearing on the right hand of the present disclosure.

Referring to FIG. 10 to FIG. 11, a diagram of a wearing state of the wristband nerve stimulator on the right hand is shown. The adapter seat 33 with pins 4, 5, 6, 9 and 10 is embedded in the adapter port 22. Pins 4, 5, 6, 9 and 10 of the adapter seat 33 are respectively connected with pins 13, 12, 11, 14 and 15 of the adapter port 22 in a contact manner. The intelligent identification unit 25 can identify whether the controller 23 is connected with pins 9 and 10 of the adapter seat 33, and ensure that the fixed main unit 20 and the electrode piece band 30 are mounted correctly. The adapter seat 33 with pins 1, 2, 3, 7 and 8 is embedded in the groove 21 and insulated. The electrode piece band 30 is fitted to the left half of the user's wrist.

When the wristband nerve stimulator is worn correctly, pin I0_2 of the controller 23 outputs a level. Pin I0_2 (pin 14) of the controller 23 is connected with the SI/O pin (pin 9) on the memory IC and performs data transmission and receiving. At this time, pin 15 (pin I0_1) of the controller 23 outputs level 0, and the communication is normal, so that it can be determined that the user wears the wristband correctly. When the wristband nerve stimulator is worn incorrectly, pin I0_2 of the controller 23 outputs a level. Pin I0_2 (pin 14) of the controller 23 is connected with the GND pin (pin 10) on the memory IC and performs data transmission and receiving. If the level of the GND pin is not 0, it can be determined that the user wears the wristband incorrectly, and the fixed main unit 20 sends a warning signal at the same time.

Further, the common electrode 16 outputs a negative current to the user, the radialis nerve electrode 17 outputs a positive current to the user, and the median nerve electrode 18 outputs a positive current to the user. The user's nerves are stimulated through different currents to achieve the electrotherapy effect.

For those skilled in the art, it is apparent that the present disclosure is not limited to the details of the demonstrative embodiments mentioned above, and that the present disclosure can be realized in other specific forms without departing from the spirit or basic features of the present disclosure. Therefore, from any point of view, the embodiments should be regarded as exemplary and non-limiting. The scope of the present disclosure is defined by the appended claims rather than the above description. Therefore, all changes falling within the meanings and scope of equivalent elements of the claims are intended to be included in the present disclosure. No drawing markings in claims shall be deemed to limit the claims involved.

What is claimed is:

1. A wristband nerve stimulator applicable to both the left and right hands, comprising:

a fixed main unit, wherein a groove and an adapter port are respectively arranged on two sides of a bottom of the fixed main unit; a controller is arranged in the fixed main unit; the controller at least comprises a main control unit (MCU), a storage unit and a stimulation unit; and an electrode piece band, wherein the electrode piece band comprises a base and an electrode assembly; adapter seats are arranged on two sides of a top surface of the base; the shapes of the two adapter seats are matched with the shapes of the groove and the adapter port;

an intelligent identification unit, wherein the intelligent identification unit can identify connection pins of a controller and a memory IC, and determines a connection direction of the electrode piece band according to preset parameters of the fixed main unit; if the connection direction is correct, the fixed main unit and the electrode piece band can be used normally; if the connection direction is wrong, the fixed main unit and the electrode piece band cannot be used, and the fixed main unit continuously sends a warning signal and cannot be used normally until the connection direction is turned;

wherein a plurality of PIN points are arranged in the adapter port; the adapter seats are provided with a plurality of pins, and three electrode pieces are provided; the three electrode pieces include a common electrode, a radialis nerve electrode and a median nerve electrode respectively; the common electrode is located below the base, the radialis nerve electrode is located in a middle portion of the electrode assembly, and the median nerve electrode is located at the outermost end of the electrode assembly; the adapter seat on the left is provided with five pins including pins 1, 2, 3, 7 and 8; the adapter seat on the right is provided with five pins including pins 4, 5, 6, 9 and 10; pins 1, 2 and 3 of the adapter seat on the left and pins 4, 5 and 6 of the adapter seat on the right are electrically connected with the radialis nerve electrode, the common electrode and the median nerve electrode; the fixed main unit and the electrode piece band are electrically connected with each other through contact between the PIN points and the pins.

2. The wristband nerve stimulator applicable to both the left and right hands according to claim 1, wherein a plurality of PIN points are arranged in the adapter port; the controller is electrically connected to the plurality of PIN points; and the controller further comprises an intelligent identification unit.

3. The wristband nerve stimulator applicable to both the left and right hands according to claim 1, wherein a memory IC is arranged in the base; the two adapter seats are electrically connected with the memory IC; an independent identification ID is arranged in the memory IC; the electrode assembly is provided with a plurality of electrode pieces; the two adapter seats are electrically connected with the plurality of electrode pieces; and a plurality of pins matched with the PIN points are arranged on the adapter seats.

4. The wristband nerve stimulator applicable to both the left and right hands according to claim 1, wherein a plurality of first magnetic attraction blocks are arranged at the bottom of the fixed main unit; the plurality of first magnetic attraction blocks are respectively located on front and rear sides of the groove and front and rear sides of the adapter port; and a plurality of second magnetic attraction blocks matched with the first magnetic attraction blocks are arranged on the base.

5. The wristband nerve stimulator applicable to both the left and right hands according to claim 1, wherein a plurality of PIN points are arranged in the adapter port; a plurality of pins are arranged on the adapter seats; and the fixed main unit is electrically connected with the electrode piece band through contact between the PIN points and the pins.

6. The wristband nerve stimulator applicable to both the left and right hands according to claim 1, wherein the intelligent identification unit is configured to identify the identification ID in the memory IC to monitor the number of use or a service life of the electrode piece band.

7. The wristband nerve stimulator applicable to both the left and right hands according to claim 1, wherein the fixed main unit is also provided with a display screen, a control button and a charging interface.

8. The wristband nerve stimulator applicable to both the left and right hands according to claim 1, further comprising a regulation band, wherein two ends of the regulation band are movably connected with two sides of the fixed main unit respectively.

9. A use method of a wristband nerve stimulator applicable to both the left and right hands, comprising:

S1: an adapter seat on one side is embedded in an adapter port; the adapter seat on the other side is embedded in a groove; a first magnetic attraction blocks and a second magnetic attraction blocks are connected in an attracting manner, so that a fixed main unit and an electrode piece band are quickly mounted; PIN points and pins are connected with each other in a resisting manner, so that the fixed main unit and the electrode piece band are electrically connected;

S2: an intelligent identification unit can identify connection pins of a controller and a memory IC, and determines a connection direction of the electrode piece band according to preset parameters of the fixed main unit; if the connection direction is correct, the fixed main unit and the electrode piece band can be used normally; if the connection direction is wrong, the fixed main unit and the electrode piece band cannot be used, and the fixed main unit continuously sends a warning signal and cannot be used normally until the connection direction is turned;

S3: the intelligent identification unit also detects the independent identification ID in the memory IC, compares a parameter in the storage unit with the identification ID, and determines whether the electrode piece band is a matched electrode piece band; if the electrode piece band is the matched electrode piece band, the fixed main unit and the electrode piece band can be used normally; if the electrode piece band is not a matched electrode piece band, the fixed main unit and the electrode piece band cannot be used, and the fixed main unit continuously sends a warning signal and can be used normally until the matched electrode piece band is replaced; the memory IC can be configured to record the number of use or service life of the electrode piece band; if the number of use or service life exceeds a preset number of use or service life, the fixed main unit cannot be used, and can be used normally only after a qualified electrode piece band is replaced;

S4: the wrist of a user passes through a ringlike opening between the fixed main unit and a regulation band, and the ringlike opening is regulated by the regulation band for wearing, so that electrode pieces on the electrode piece band are fully fitted to the skin of the user; and S5: the fixed main unit is controlled by a human-machine interface on the fixed main unit to output a current to the electrode piece band, and the electrode pieces generate a current to perform electrotherapy on the user.

* * * * *